US008058790B2

(12) United States Patent
Buesing et al.

(10) Patent No.: US 8,058,790 B2
(45) Date of Patent: Nov. 15, 2011

(54) MATERIAL MIXTURES FOR USE IN ELECTROLUMINESCENCE

(75) Inventors: Arne Buesing, Frankfurt am Main (DE); René Scheurich, Gross-Zimmern (DE); Susanne Heun, Bad Soden (DE); Ingrid Bach, Hofheim (DE)

(73) Assignee: Merck Patent GmbH, Darmstadt (DE)

( * ) Notice: Subject to any disclaimer, the term of this patent is extended or adjusted under 35 U.S.C. 154(b) by 1092 days.

(21) Appl. No.: 11/596,210

(22) PCT Filed: May 10, 2005

(86) PCT No.: PCT/EP2005/005021
§ 371 (c)(1),
(2), (4) Date: Dec. 7, 2006

(87) PCT Pub. No.: WO2005/111172
PCT Pub. Date: Nov. 24, 2005

(65) Prior Publication Data
US 2007/0176147 A1 Aug. 2, 2007

(30) Foreign Application Priority Data
May 11, 2004 (DE) .......................... 10 2004 023 277

(51) Int. Cl.
*H01J 1/62* (2006.01)
(52) U.S. Cl. ................... 313/483; 313/504; 252/301.16; 252/301.35; 428/690; 428/917; 525/474; 528/25
(58) Field of Classification Search .................. None
See application file for complete search history.

(56) References Cited

U.S. PATENT DOCUMENTS

| | | |
|---|---|---|
| 6,994,893 B2 | 2/2006 | Spreitzner et al. |
| 7,094,897 B2 | 8/2006 | Stossel et al. |
| 7,125,998 B2 | 10/2006 | Stossel et al. |
| 7,473,477 B2 * | 1/2009 | Ren et al. ............... 428/690 |
| 2002/0028329 A1 | 3/2002 | Ise et al. |
| 2003/0120124 A1 | 6/2003 | Spivak |
| 2004/0135131 A1 | 7/2004 | Treacher et al. |
| 2004/0206939 A1 | 10/2004 | Spreitzer et al. |
| 2005/0038223 A1 | 2/2005 | Becker et al. |
| 2005/0064238 A1 | 3/2005 | Lee et al. |
| 2005/0238919 A1 | 10/2005 | Ogasawara |
| 2006/0058494 A1 | 3/2006 | Busing et al. |
| 2006/0127696 A1 | 6/2006 | Stossel et al. |
| 2007/0257604 A1 * | 11/2007 | Kamatani et al. ......... 313/504 |

FOREIGN PATENT DOCUMENTS

| | | |
|---|---|---|
| DE | 103 50 606 | 6/2005 |
| EP | 1 239 526 | 9/2002 |
| JP | 2002100476 A | 4/2002 |
| JP | 2003243178 A | 8/2003 |
| JP | 2003321546 A | 11/2003 |
| JP | 2004303636 A | 10/2004 |
| JP | 2005097301 A | 4/2005 |
| JP | 2005-310672 A | 11/2005 |
| JP | 2005314689 A | 11/2005 |
| WO | WO-90/13148 | 11/1990 |
| WO | WO-99/21935 | 5/1999 |
| WO | WO-01/59030 | 8/2001 |
| WO | WO-02/066552 | 8/2002 |
| WO | WO-02/068435 | 9/2002 |
| WO | WO-02/072714 | 9/2002 |
| WO | WO-02/077060 | 10/2002 |
| WO | WO-02/081488 | 10/2002 |
| WO | WO-03/019694 | 3/2003 |
| WO | WO-03/020790 | 3/2003 |
| WO | WO 03/022908 * | 3/2003 |
| WO | WO-03/048224 | 6/2003 |
| WO | WO-03/092334 | 11/2003 |
| WO | WO-2004/015025 | 2/2004 |
| WO | WO-2004/026886 | 4/2004 |
| WO | WO-2004/037887 | 5/2004 |
| WO | WO-2005/014689 | 2/2005 |

OTHER PUBLICATIONS

"Phosphorescent Emission from Polymeric Light-Emitting Diodes Doped with Chrysene-d12" authored by Blumstengel et al. and published in the Japanese Journal of Applied Physics (1999) vol. 28, p. L403-L405.*
"Electroluminescence from Polysilane Film Doped with Europium Complex" authored by Kido et al., and published in Chemistry Letters (1991) 1267-1270.*
"Ultrahigh Energy Gap Hosts in Deep Blue Organic Electrophosphorescent Devices" authored by Ren et al. and published in Chemistry of Materials (2004) 16, 4743-4747.*
Definition of "alkyl" taken from the Hawley's Condensed Chemical Dictionary, 14$^{th}$ Edition (2002).*
Definition of "alkoxy" from Wikipedia (no date).*
Wong, W.-Y. et al., "Triplet Emission in Platinum-Containing Poly(alkynylsilanes)", Macromolecules 36 (2003), pp. 983-990.

* cited by examiner

*Primary Examiner* — Marc Zimmer
(74) *Attorney, Agent, or Firm* — Connolly Bove Lodge & Hutz LLP

(57) ABSTRACT

The invention relates to mixtures comprising at least one polymer, additionally comprising structural units containing at least one element from the 4$^{th}$ main group different from carbon and additionally comprising structural units that are triplet emissives. The inventive materials are better suited to the use in phosphorescent organic light emitting diodes than comparable prior art materials.

20 Claims, No Drawings

MATERIAL MIXTURES FOR USE IN ELECTROLUMINESCENCE

RELATED APPLICATIONS

This application is a national stage application (under 35 U.S.C. 371) of PCT/EP2005/005021 filed May 10, 2005, which claims benefit of German application 10 2004 023 277.6 filed May 11, 2004.

Broadly based research on the commercialisation of display and illumination elements based on polymeric (organic) light-emitting diodes (PLEDs) has been underway for about 13 years. This development was initiated by the basic developments disclosed in WO 90/13148. A first product in the form of a relatively small display (in a razor from PHILIPS N.V.) has recently also been available on the market. However, significant improvements are still necessary in order to make these displays a true competitor to the liquid-crystal displays which currently dominate the market.

A development which has been evident for some years, especially in the area of "small molecule" displays, is the use of materials which are able to emit light from the triplet state and thus exhibit phosphorescence instead of fluorescence (M. A. Baldo et al., *Appl. Phys. Lett.* 1999, 75, 4-6), enabling an up to four-fold increase in energy and power efficiency. Essential conditions for practical utility which may be mentioned here are, in particular, efficient energy transfer from the matrix to the triplet emitter (and consequently efficient light emission), a long operating lifetime and a low operating voltage.

There have recently increasingly been efforts to utilise the advantages of vapour-depositable triplet emitters for polymer applications too. Thus, consideration is being given to so-called hybrid device structures, which combine the advantages of "small molecule" OLEDs with those of polymeric OLEDs (=PLEDs) and are formed by mixing the triplet emitter into the polymer. This has the advantage that the compounds can be processed from solution and that an expensive and complex vapour-deposition process, as for devices based on low-molecular-weight compounds, is not necessary. Application from solution (for example by means of high-resolution printing processes) will have significant advantages in the long term over the vacuum evaporation process which is common today, especially with respect to scalability, structurability, coating efficiency and economy. A suitable matrix material which facilitates efficient energy transfer to the triplet emitter and, in combination with this good lifetime, has low operating voltages is also necessary here. In spite of the advances achieved recently in this area, there is still considerable potential for improvement for corresponding materials in the area of soluble triplet emitters. A clear need for improvement is furthermore to be seen, inter alia, in the following fields:

(1) The efficiency of the electroluminescent elements must be improved further. The fact that higher efficiency is possible in principle is shown by the results of electroluminescent elements based on small molecules.
(2) The voltage of the electroluminescent elements is still too high for high-quality electronic applications.
(3) Matrix materials which exhibit good results with a triplet emitter frequently exhibit significantly worse results with other emitters, even for a comparable emission colour. It would be desirable to have available a universal matrix material which gives good results for a multiplicity of triplet emitters used and if possible also for several or all emission colours.

It is thus apparent that there continues to be a great need for improvement in the area of soluble triplet emitters and corresponding suitable matrix materials.

Surprisingly, it has been found that—hitherto unknown—polymer mixtures which contain certain structural units in combination with triplet emitters give rise to significant improvements here compared with mixtures in accordance with the prior art. In particular, these materials are suitable for exhibiting efficient emission with a wide range of different red- and green-emitting triplet emitters. The present application therefore relates to these mixtures.

The invention relates to mixtures (blends) comprising (A) at least one polymer, (B) at least one structural unit which contains at least one element from main group 4 (group 14 in accordance with IUPAC) other than carbon, i.e. silicon, germanium, tin and/or lead, and (C) at least one triplet emitter.

The mixtures according to the invention are preferably in the form of amorphous mixtures.

For the purposes of the invention, a triplet emitter is intended to be taken to mean a compound which emits light from the triplet state, i.e. exhibits phosphorescence instead of fluorescence in the electroluminescence, preferably an organometallic triplet emitter.

Preferred structural units which contain at least one element from main group 4 other than carbon contain direct silicon-silicon or germanium-germanium bonds, and/or contain at least one sub-structure of the formula (1):

A-Y                                                                  formula (1), where the following applies to the symbols:

A is on each occurrence, identically or differently, Si, Ge, Sn or Pb;

Y is on each occurrence, identically or differently, an aromatic or heteroaromatic ring system having 2 to 40 C atoms, which may be substituted by one or more radicals R$^4$, a vinyl group —CR$^4$=CR$^4$— or —CR$^4$=C(R$^4$)$_2$, an acetylene group —C≡C— or —C≡CR$^4$ or a combination of 2 to 5 of these groups, such as, for example, a stilbene group or a tolan group; Y here stands for a monovalent or divalent group;

R$^4$ is on each occurrence, identically or differently, H, F, Cl, Br, I, CN, OH, NO$_2$, a straight-chain, branched or cyclic alkyl, alkoxy or thioalkoxy group having 1 to 22 C atoms, in which, in addition, one or more non-adjacent C atoms may be replaced by —R$^5$C=CR$^5$—, —C≡C—, Si(R$^5$)$_2$, Ge(R$^5$)$_2$, Sn(R$^5$)$_2$, —NR$^5$—, —O—, —S—, —CO—O—, —O—CO—O—, where, in addition, one or more H atoms may be replaced by F, Cl, Br, I, CN or NO$_2$, an aryl, heteroaryl or aryloxy group having 1 to 40 C atoms, which, in addition, may be substituted by one or more radicals R$^5$, or OH, N(R$^5$)$_2$, B(R$^5$)$_2$ or Si(R$^5$)$_3$;

R$^5$ is on each occurrence, identically or differently, H or an aliphatic or aromatic hydrocarbon radical having 1 to 20 C atoms.

Particularly preferred structural units which contain at least one element from main group 4 other than carbon contain at least one structural unit of the formulae (2) to (5)

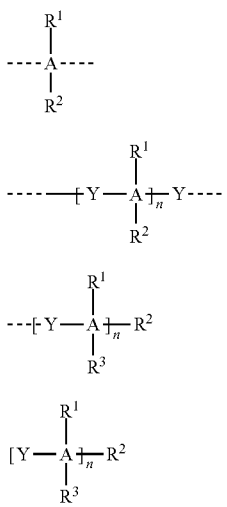

Formula (2)
Formula (3)
Formula (4)
Formula (5)

where the symbols A, Y, $R^4$ and $R^5$ have the same meaning as described under formula (1); Y stands for divalent groups in the formulae (3) and (4) and for a monovalent group in formula (5); the other symbols have the following meaning:

$R^1$, $R^2$, $R^3$ is on each occurrence, identically or differently, H, F, CN, $N(R^4)_2$, a straight-chain, branched or cyclic alkyl, alkoxy or thioalkoxy group having 1 to 40 C atoms, which may be substituted by $R^4$, where one or more non-adjacent $CH_2$ groups may be replaced by $-R^5C=CR^5-$, $-C\equiv C-$, $Si(R^5)_2$, $Ge(R^5)_2$, $Sn(R^5)_2$, $C=O$, $C=S$, $C=Se$, $C=NR^5$, $-O-$, $-S-$, $-NR^5-$ or $-CONR^5-$ and where one or more H atoms may be replaced by F, Cl, Br, I, CN, OH or $NO_2$, or an aromatic or heteroaromatic ring system or an aryloxy or heteroaryloxy group, in each case having 2 to 40 aromatic C atoms, where one or more H atoms may be replaced by F, Cl, Br, I, CN, OH or $NO_2$ or which may be substituted by one or more radicals $R^4$, or a combination of 2 to 5 of these systems, such as, for example, a stilbene group, an alkylaryl group or a tolan group; two or more substituents $R^1$, $R^2$ and/or $R^3$ here may define a further mono- or polycyclic, aliphatic or aromatic ring system with one another;

n is on each occurrence, identically or differently, 1, 2, 3 or 4; the dashed bond represents the link to the polymer; it is not intended to denote a methyl group here.

Polymers which contain units of the formula (2) can have direct bonds between two or more elements A.

A suitable ratio of the individual components is, for example, a mixture which contains in total 1-99.5 mol %, preferably 5-80 mol %, particularly preferably 10-50 mol %, of units of the formula (1) or of the formulae (2) to (5) and 0.1-95 mol %, preferably 0.5-80 mol %, particularly preferably 1-50 mol %, in particular 2-25 mol %, of one or more triplet emitters, where the data relate to all the units present (blend constituents or recurring units in the polymer). This is independent of whether the components are covalently bonded to a polymer or mixed in.

It has been found here that, in particular, a proportion of 10-50 mol % of units of the formula (1) or of the formulae (2) to (5) results in high light emission from the triplet emitter.

In the case of the mixtures according to the invention, there are various embodiments in which the units of the formula (1) and/or the triplet emitter are either mixed in or covalently bonded to the polymer. Units of the formulae (2) to (4) are covalently bonded to the polymer here. Formula (5) shows mixed-in units. In the case of covalent bonding to the polymer, the element A (i.e. the element from main group 4 other than carbon) can either be bonded into the main chain (formulae 2 and 3) or into the side chain (formula 4) of the polymer.

For the purposes of this invention, an aromatic or heteroaromatic ring system is intended to be taken to mean a system which does not necessarily contain only aromatic or heteroaromatic groups, but instead in which, in addition, a plurality of aromatic or heteroaromatic groups may be interrupted by a short non-aromatic unit (less than 10% of the atoms other than H, preferably less than 5% of the atoms other than H), such as, for example, $sp^3$-hybridised C, O, N, etc. Thus, for example, systems such as 9,9'-spirobifluorene, 9,9-diarylfluorene, triarylamine, diaryl ether, etc. are also intended to be taken to mean aromatic systems. An aromatic ring system here contains at least 6 C atoms, while a heteroaromatic ring system contains at least 2 C atoms and at least one hetero atom, preferably selected from N, O and/or S, and the total number of C atoms and hetero atoms is at least 5.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethyl-hexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. A $C_2$-$C_{40}$-aryl or -heteroaryl group, which may be monovalent or divalent depending on the use and which may in each case also be substituted by the above-mentioned radicals $R^1$ and linked to the aromatic or heteroaromatic radical via any desired positions, is taken to mean, in particular, groups which are derived from benzene, naphthalene, anthracene, phenanthrene, pyrene, chrysene, perylene, fluoranthene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazineimidazole, quinoxalineimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thia-diazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. Aromatic ring systems are furthermore taken to mean, in particular, biphenylene, terphenylene, fluorene, spirobifluorene, dihydrophenanthrene, dihydropyrene, tetrahydropyrene or cis- or trans-indenofluorene.

One embodiment of the invention are mixtures BLEND1 comprising (A) 5-99.9% by weight of at least one polymer POLY1 containing 1-100 mol %, preferably 5-80 mol %, particularly preferably 10-50 mol %, of one or more recurring units of the formula (1) or of the formulae (2) to (4), and in addition (B) 0.1-95% by weight, preferably 0.5-80% by weight, particularly preferably 1-50% by weight, in particular 2-25% by weight, of one or more triplet emitters (TRIP1).

In the embodiment BLEND1, the triplet emitter (TRIP2) is mixed with the polymer POLY1. The recurring units of the formula (1) or of the formulae (2) to (4) are co-valently bonded to the polymer. Depending on the linking, these structural units are incorporated into the main chain of the polymer (formulae 2 and 3) or into the side chain (formula 4) of the polymer.

A further embodiment of this invention are mixtures BLEND2 comprising (A) 0.5-99% by weight of at least one polymer POLY2 containing 0.1-100 mol % of one or more covalently bonded triplet emitters (TRIP2), and in addition (B) 1-99.5% by weight of at least one compound of the formula (1) or of the formula (5) which is capable of forming glass-like layers at room temperature, preferably having a glass transition temperature of greater than 80° C., particularly preferably greater than 100° C.

The triplet emitter TRIP2 here can be incorporated into the main chain and/or into the side chain of the polymer POLY2.

A further embodiment of this invention are mixtures BLEND3 comprising (A) 0.5-98.5% by weight of at least one polymer POLY3;

(B) 1-99% by weight of at least one compound of the formula (1) or of the formula (5) which is capable of forming glass-like layers at room temperature, preferably having a glass transition temperature of greater than 80° C., particularly preferably greater than 100° C.;

and in addition (C) 0.1-95% by weight, preferably 0.5-80% by weight, particularly preferably 1-50% by weight, in particular 2-25% by weight, of one or more triplet emitters (TRIP1).

The polymers POLY1 to POLY3 may be conjugated, partially conjugated or non-conjugated. They are preferably conjugated or partially conjugated.

For the purposes of this invention, conjugated polymers are polymers which contain principally $sp^2$-hybridised (or also sp-hybridised) carbon atoms, which may also be replaced by corresponding hetero atoms, in the main chain. In the simplest case, this means the alternating presence of double and single bonds in the main chain. Principally means that defects occurring naturally (without further assistance) which result in conjugation interruptions do not devalue the term "conjugated polymer". Furthermore, the term conjugated is likewise used in this application text if arylamine units, arylphosphine units and/or certain heterocyclic units (i.e. conjugation via N, O, S or P atoms) and/or organometallic complexes, such as, for example, TRIP2 units (conjugation via the metal atom), are located in the main chain. The term conjugated is likewise used for so-called σ-conjugation, i.e., for example, conjugation via a silicon atom. For the purposes of this invention, partially conjugated polymers are polymers which either contain relatively long conjugated sections interrupted by non-conjugated sections in the main chain or contain relatively long conjugated sections in the side chains of a polymer which is non-conjugated in the main chain. By contrast, units such as, for example, simple alkylene chains, (thio)ether bridges, ester, amide or imide links would clearly be defined as non-conjugated segments.

In addition to the units of the formula (1) or of the formulae (2) to (4) (in POLY1) and triplet emitter TRIP2 (in POLY2), polymers POLY1, POLY2 and POLY3 may contain various further structural elements. These may be, for example, structural units which are able to form the polymer backbone or structural units which improve the charge-injection or charge-transport properties. Units of this type are described in detail, for example, in WO 03/020790 and in WO 05/014689.

If polymers POLY1, POLY2 or POLY3 are non-conjugated polymers, any desired classes of compound are in principle suitable therefor so long as the polymers have adequate solubility in a solvent or solvent mixture in which the other blend constituents are also soluble, so that all components can be processed jointly from solution.

Polymers POLY1, POLY2 and POLY3 are either homopolymers, i.e. they contain only a single monomer structure, or they are copolymers. The copolymers can have random, alternating or also block-like structures or also have a plurality of these structures in an alternating arrangement. The polymers may also have a linear, branched or dendritic structure. The use of a plurality of different structural elements enables properties such as, for example, solubility, solid-phase morphology, etc. to be adjusted.

Polymers POLY1, POLY2 and POLY3 are prepared by polymerisation of one or more monomers. In particular for the synthesis of conjugated polymers, some types which result in C—C links (SUZUKI coupling, YAMAMOTO coupling, STILLE coupling) or in C—N links (HARTWIG-BUCHWALD coupling) have proven successful here. The way in which the polymerisation can be carried out by these methods and the way in which the polymers can be separated off from the reaction medium and purified is described in detail, for example, in WO 04/037887. A method for the formation of silicon-aryl bonds is described in US 2003/0120124 and consists in the reaction of aryldiazonium salts with substituted chlorosilanes.

The synthesis of partially conjugated or non-conjugated polymers can also be carried out by these methods by using corresponding monomers which are not continuously conjugated. For partially conjugated or non-conjugated polymers, however, other synthetic methods are also suitable, as are generally familiar from polymer chemistry, such as, for example, polycondensation or cationic, anionic or free-radical polymerisation, which proceeds, for example, via the reaction of alkenes and results in polyethylene derivatives in the broadest sense, such as, for example, polystyrene derivatives, etc., which contain the chromophores optionally bonded in the side chains. Polysilanes can be produced, for example, by the Wurtz synthesis by reaction of correspondingly substituted dichlorosilanes with metallic sodium.

In a preferred embodiment of the invention, the symbol A on each occurrence, identically or differently, stands for Si or Ge, very particularly preferably for Si.

The symbol Y furthermore preferably stands, identically or differently on each occurrence, for an aromatic ring system having 2 to 40 C atoms, which may be substituted by one or more radicals $R^4$, or a stilbene or tolan group which is substituted by $R^4$ or is unsubstituted, very particularly preferably for an aromatic ring system having 2 to 20 C atoms, which may be substituted by one or more radicals $R^4$.

At least one of the substituents $R^1$ to $R^3$ furthermore preferably stands for an aromatic ring system having 2 to 40 C atoms, which may be substituted by one or more substituents $R^4$; particularly preferably, all substituents $R^1$ to $R^3$ stand for aromatic ring systems, each having 2 to 20 C atoms, which may be substituted by one or more substituents $R^4$.

The index n is furthermore preferably on each occurrence, identically or differently, 1, 2 or 3, particularly preferably 1 or 2.

Units of the formulae (2) to (5) furthermore preferably have a symmetrical structure. This preference is due to the easier synthetic accessibility of these compounds. For compounds of the formula (2), $R^1$ is thus preferably=$R^2$. For compounds of the formula (3), it is preferred that all Y are selected to be the same and that all $R^1$=$R^2$. For compounds of the formula (4), it is preferred that $R^1$=$R^2$=$R^3$. For compounds of the formula (5), it is preferred that $R^1$=$R^2$=$R^3$ and optionally=Y.

Examples of preferred units of the formulae (2) to (5) are substituted or unsubstituted structures in accordance with Examples (1) to (48) shown, where the dashed bonds denote a link in the polymer; Examples (1) to (6) here are examples of the general formula (2), Examples (7) to (21) are examples of the general formula (3), Examples (22) to (33) are examples of the general formula (4), Examples (34) to (48) are examples of the general formula (5). Alkyl stands for a straight-chain, branched or cyclic alkyl chain, which may be substituted or unsubstituted and in which one or more H atoms may be replaced by fluorine, as defined for $R^1$, $R^2$ and $R^3$. Potential substituents are generally not shown for better clarity.

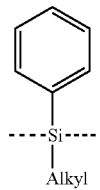

Example 1

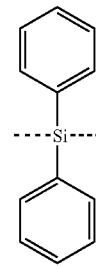

Example 2

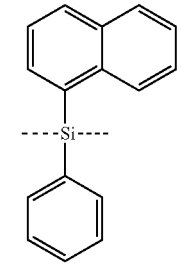

Example 3

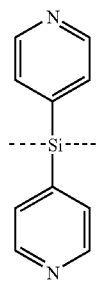

Example 4

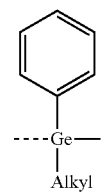

Example 5

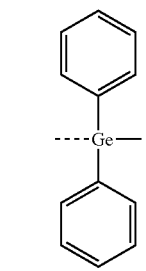

Example 6

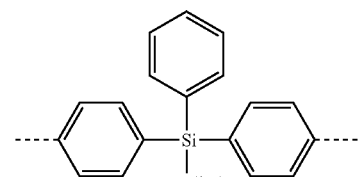

Example 7

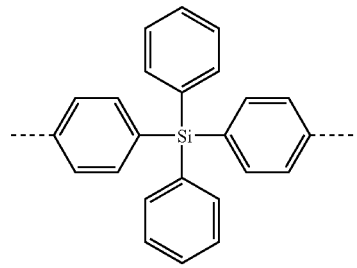

Example 8

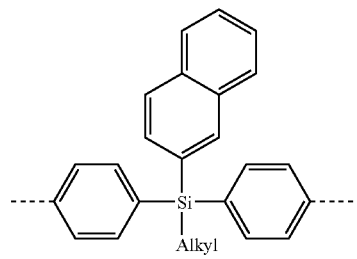

Example 9

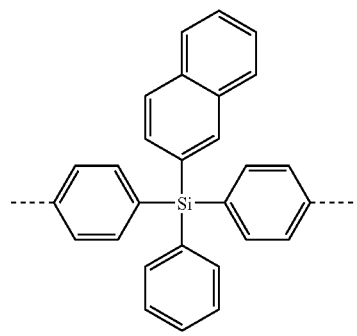

Example 10

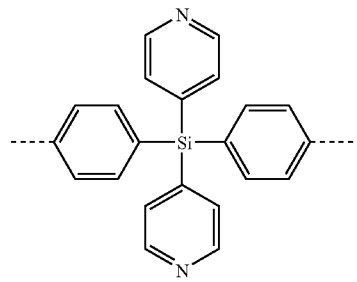

Example 11

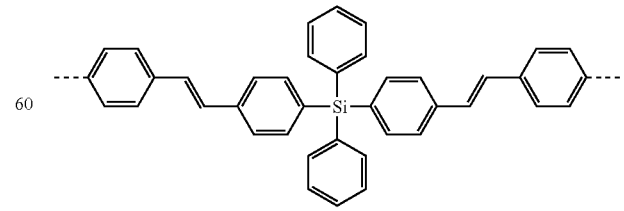

Example 12

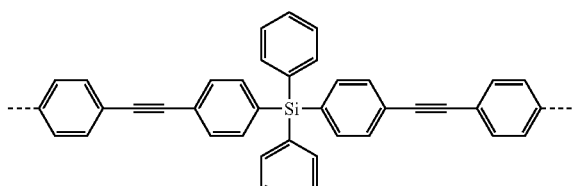
Example 13
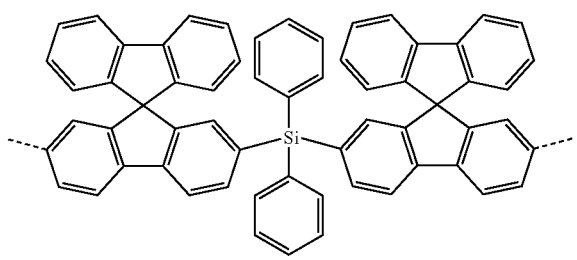
Example 14
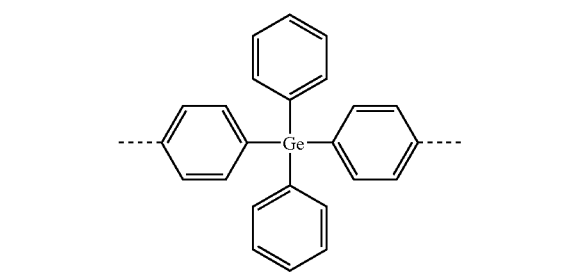
Example 15
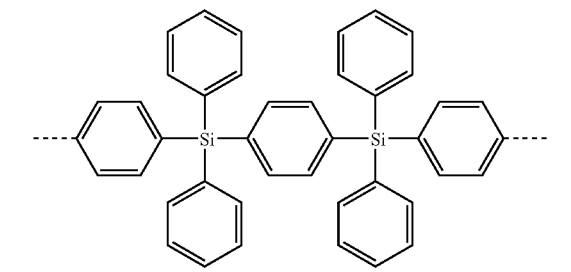
Example 16
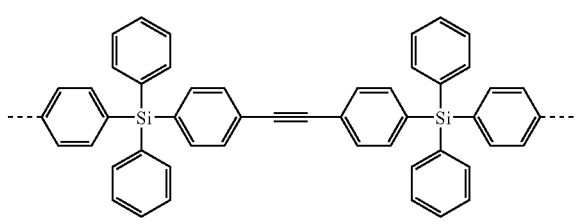
Example 17
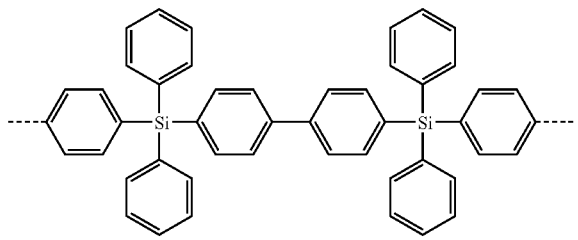
Example 18
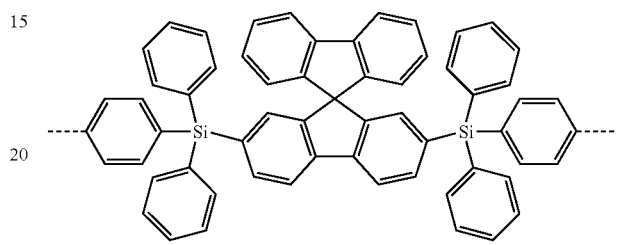
Example 19
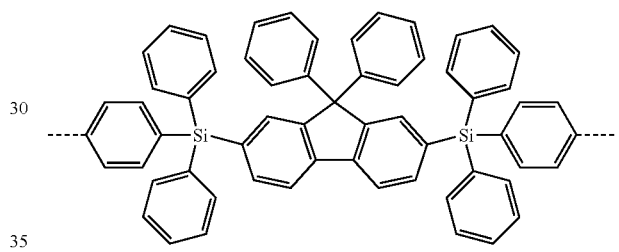
Example 20
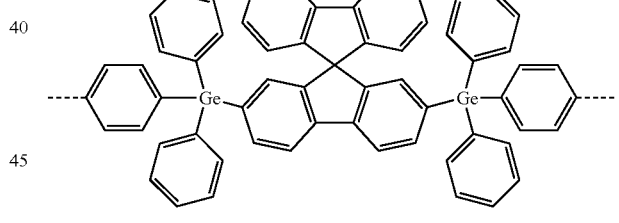
Example 21
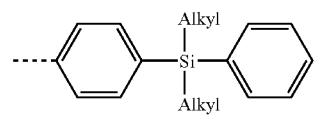
Example 22
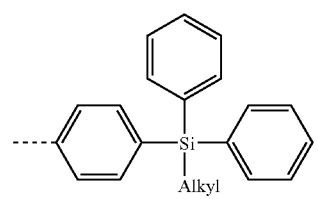
Example 23

-continued
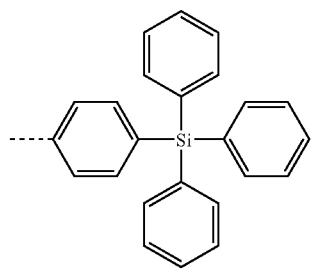
Example 24
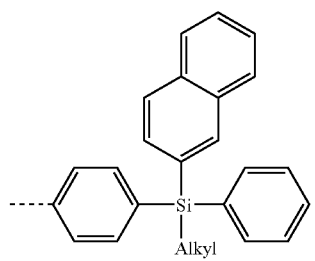
Example 25
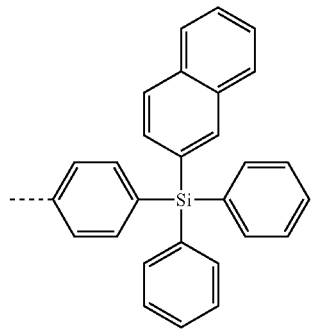
Example 26
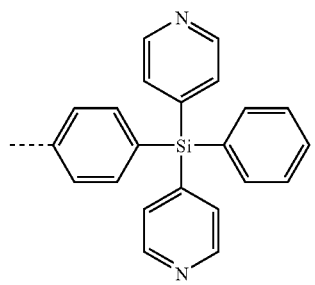
Example 27
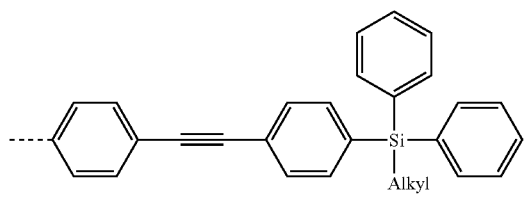
Example 28
-continued
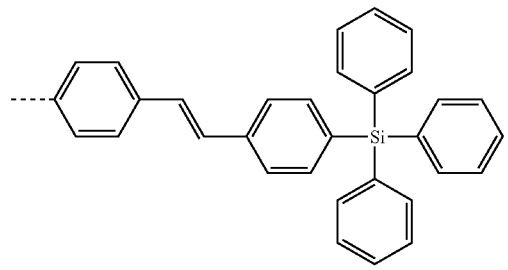
Example 29
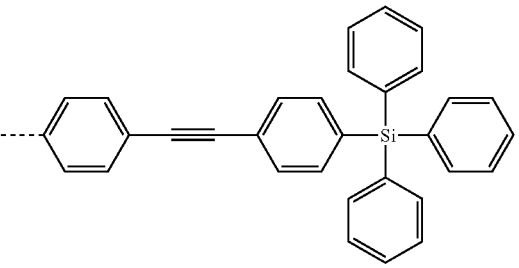
Example 30
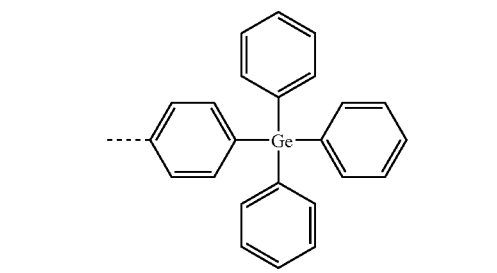
Example 31
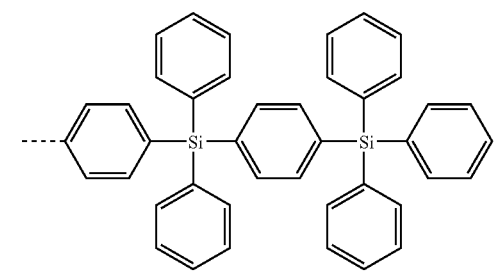
Example 32
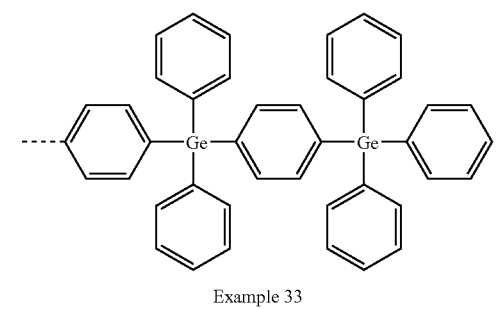
Example 33

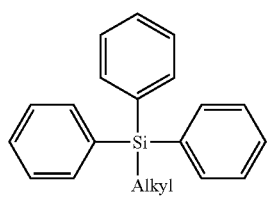
Example 34
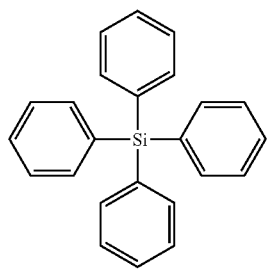
Example 35
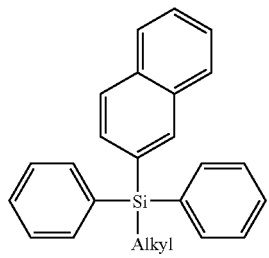
Example 36
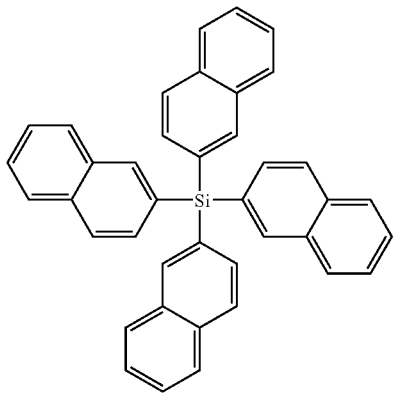
Example 37
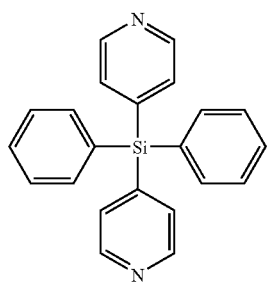
Example 38
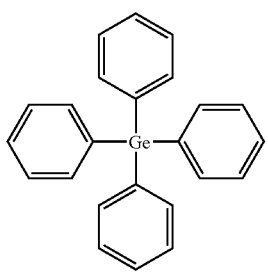
Example 39
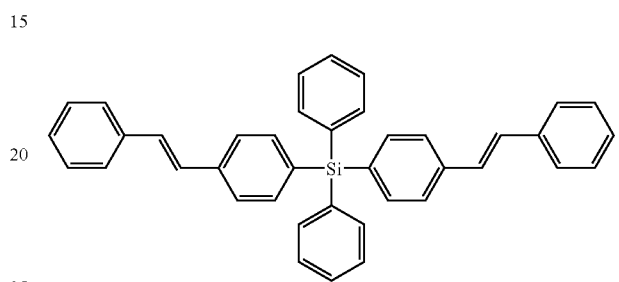
Example 40
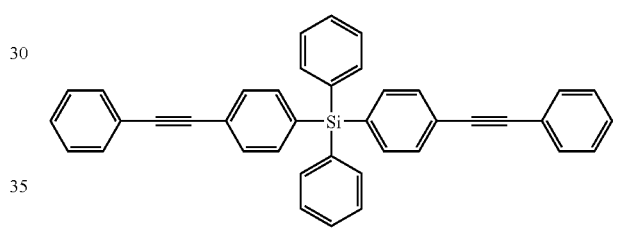
Example 41
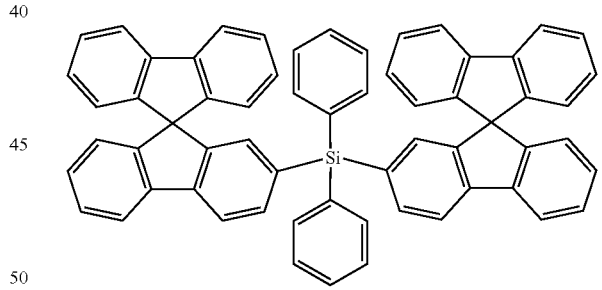
Example 42
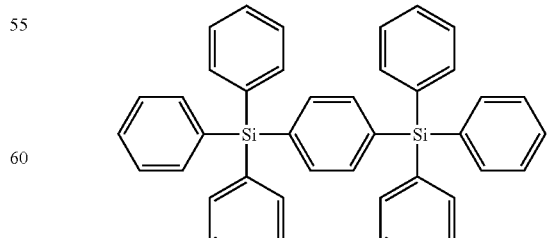
Example 43

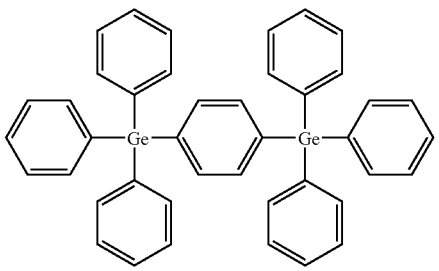

Example 44

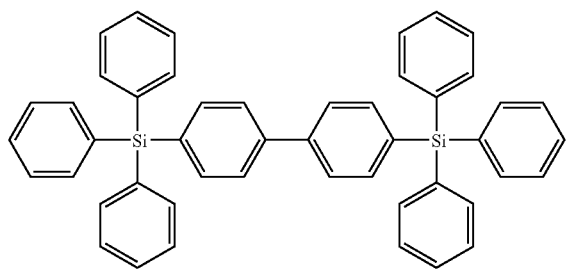

Example 45

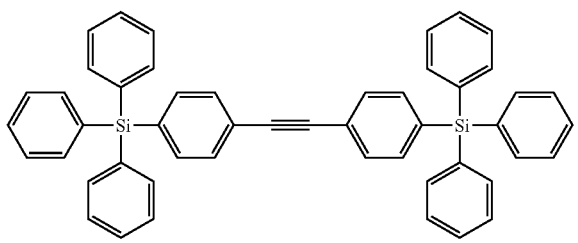

Example 46

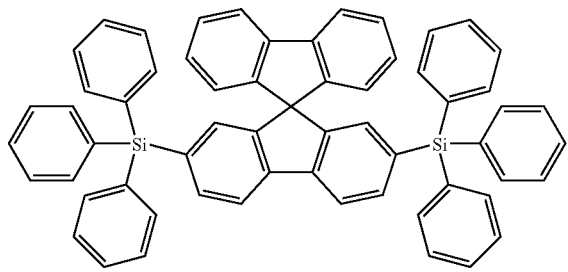

Example 47

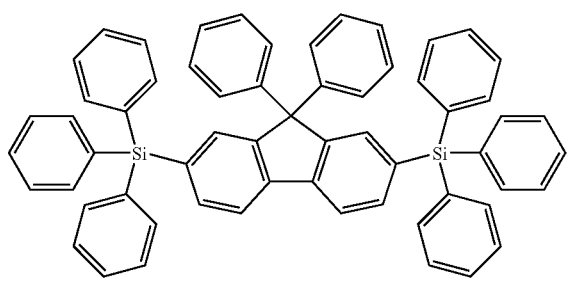

Example 48

Although evident from the description, it should again explicitly be pointed out here that the structural units from Examples (1) to (48) may also be asymmetrically substituted, i.e. different substituents $R^4$ may be present on one unit or may also be bonded in different positions. In the case of prochiral structural units, all tacticity or chirality possibilities are encompassed.

The structural units of the formulae (2) to (4) are a covalent constituent of the matrix polymer POLY1. It has been found that a proportion in the range 1-100 mol % of these recurring units (based on all recurring units in the polymer) achieves good results here. A proportion of 1-100 mol % of recurring units of the formulae (2) to (4) is preferred for POLY1. A proportion of 5-80 mol % of recurring units of the formulae (2) to (4) is particularly preferred, a proportion of 10-50 mol % of recurring units of the formulae (2) to (4) is very particularly preferred.

Compounds of the formula (5) are a mixture constituent of BLEND2 and BLEND3. It has been found that a proportion in the range 1-99% by weight of these compounds in the mixture achieves good results here. A proportion of 1-99% by weight of compounds of the formula (5) is preferred for BLEND2 and BLEND3. A proportion of 5-80% by weight of the formula (5) is particularly preferred, a proportion of 10-50% by weight of the formula (5) is very particularly preferred.

A further aspect of the invention is the mixing of compounds of the formula (5) into BLEND1. It has been found here that a total proportion of 1-99 mol % of structural units of the formula (1) or of the formulae (2) to (5) achieves good results, irrespective of whether these units are covalently bonded to the polymer or are mixed in. Preference is thus given here to a total proportion of 1-99 mol % of structural units of the formula (1) or of the formulae (2) to (5). Particular preference is given to a total proportion of 5-80 mol % of structural units of the formula (1) or of the formulae (2) to (5), very particular preference is given to a total proportion of 10-50 mol % of structural units of the formula (1) or of the formulae (2) to (5).

The triplet emitters TRIP1 mixed into BLEND1 and BLEND3 and the triplet emitters TRIP2 copolymerised into POLY2 (=BLEND2) can be selected from various organometallic or inorganic classes of substance which are able to emit light from the triplet state at room temperature, i.e. exhibit phosphorescence instead of fluorescence: these are firstly, in particular, compounds which contain heavy atoms, i.e. atoms from the Periodic Table of the Elements having an atomic number of greater than 36. Particularly suitable for this purpose are compounds containing d and f transition metals which satisfy the above-mentioned condition. Very particular preference is given here to corresponding structural units which contain elements from groups 8 to 10 (Ru, Os, Rh, Ir, Pd, Pt). Without wishing to be tied to a specific theory, all emitting compounds which contain these elements are regarded as triplet emitters for the purposes of this application.

The triplet emitters TRIP1 can be low-molecular-weight, oligomeric, dendritic or polymeric compounds. Since they are processed as mixture constituent (BLEND1 or BLEND3), they must have adequate solubility in suitable solvents (for example toluene, xylene, anisole, THF, etc.) in order that processing from solution is possible. Suitable low-molecular-weight structural units are various complexes which are described, for example, in the application specifications WO 02/068435, WO 02/081488, EP 1239526 and WO 04/026886. Suitable dendritic structures for TRIP1 and TRIP3 are complexes as described, for example, in the application specifications WO 99/21935, WO 01/059030 and WO 02/066552.

Triplet emitter TRIP2 is incorporated covalently into the polymer chain of POLY2 (BLEND2). In order to facilitate the incorporation of TRIP2 into POLY2, functional polymerisable groups must be present on TRIP2. Examples of corresponding brominated complexes which can be employed as monomers in polycondensations (for example in accordance with SUZUKI or in accordance with YAMAMOTO) are described in WO 02/068435 and in the as yet unpublished application DE 10350606.3.

Mixture BLEND1 according to the invention is obtained by admixing a triplet emitter TRIP1 with polymer POLY1.

Mixture BLEND2 according to the invention is obtained by admixing a compound of the formula (5) with polymer POLY2.

Mixture BLEND3 according to the invention is obtained by admixing a compound of the formula (5) and a triplet emitter TRIP1 with polymer POLY3.

It may in addition be preferred to mix further conjugated, partially conjugated or non-conjugated polymers, oligomers, dendrimers or further low-molecular-weight compounds into BLEND1 to BLEND3. The addition of further components may prove appropriate for some applications: thus, the hole or electron injection, the hole or electron transport or the charge equilibrium in the corresponding blend can be regulated, for example, by addition of an electronically active substance. The added component may also improve singlet-triplet transfer. However, the addition of electronically inert compounds may also be helpful in order, for example, to control the viscosity of a solution or the morphology of the film formed. The invention likewise relates to the blends obtained in this way.

The preparation of BLEND1 to BLEND3 is carried out as follows: the individual constituents are combined in a suitable mixing ratio and dissolved in a suitable solvent system. Suitable solvents are, for example, toluene, anisole, xylenes, methylanisole, methylnaphthalene, chlorobenzene, cyclic ethers (for example dioxane, THF, methyidioxane), amides (for example NMP, DMF) or mixtures of these solvents. Alternatively, the constituents of the blend may also be dissolved individually. In this case, the solution of the blend is obtained by combining the individual solutions in the suitable mixing ratio. The dissolution operation here is preferably carried out in an inert atmosphere and where necessary at elevated temperature. The blend is generally not isolated as solid (by repeated precipitation), but instead processed further directly from solution.

A suitable ratio of the individual components is, for example, a mixture which contains in total 1-99.5 mol %, preferably 5-80 mol %, particularly preferably 10-50 mol %, of units of the formula (1) or of the formulae (2) to (5) and 0.1-95 mol %, preferably 0.5-80 mol %, particularly preferably 1-50 mol %, in particular 2-25 mol %, of TRIP1 and/or TRIP2, where the data relate to all the units present (blend constituents or recurring units in the polymer). This is irrespective of whether the components are covalently bonded to a polymer or mixed in.

Mixtures BLEND1 to BLEND3 according to the invention have the following surprising advantages over the prior art:
- The efficiency of light emission by the triplet emitter is better in mixtures BLEND1 to BLEND3 according to the invention compared with mixtures in accordance with the prior art.
- The voltages for operation of the light-emitting diode are lower compared with the prior art.
- With the aid of the novel mixtures, efficient triplet devices are possible from solution for a wide range of red and green triplet emitters. This is a surprising result since, in accordance with the prior art, specific matrices are generally required for the individual colours (and in some cases even for different emitters of comparable colour).

The invention furthermore relates to solutions and formulations of a blend according to the invention in one or more solvents. The way in which solutions of this type can be prepared is described, for example, in WO 02/072714, in WO 03/019694 and in the literature cited therein. These solutions can be used to produce thin polymer layers, for example by area-coating processes (for example spin coating) or printing processes (for example ink-jet printing).

Mixtures BLEND1 to BLEND3 can be used in PLEDs, in particular as electro-luminescent materials (=emitting materials). For the construction of PLEDs, use is generally made of a general process which should be adapted correspondingly for the individual case. A process of this type has been described in detail, for example, in WO 04/037887.

The invention therefore also relates to the use of a mixture BLEND1 to BLEND3 according to the invention as electroluminescent material in a PLED.

The invention likewise relates to a PLED having one or more layers, where at least one of these layers, preferably an emission layer, comprises at least one mixture BLEND1, BLEND2 and/or BLEND3 according to the invention.

The present application text and the examples below are directed to the use of mixtures BLEND1 to BLEND3 according to the invention in relation to PLEDs and the corresponding displays. In spite of this restriction of the description, it is possible for the person skilled in the art, without further inventive step, also to use the polymers or blends according to the invention for further uses in other electronic devices, for example for organic solar cells (O-SCs), non-linear optics, frequency doubling (up-conversion), organic optical detectors, organic field-quench devices (O-FQDs) or also organic laser diodes (O-lasers), to mention but a few applications. The present invention also relates to these.

The invention is explained in greater detail by the following examples without wishing to be restricted thereby.

EXAMPLES

Example 1

Synthesis of 4,4'-dibromotetraphenylsilane (monomer Si1)

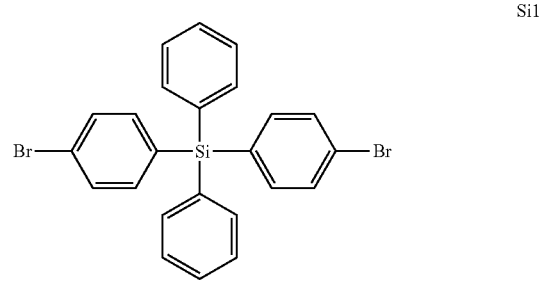

33.9 g (144 mmol) of 1,4-dibromobenzene were dissolved in 300 ml of absolute THF in a 1000 ml four-necked flask which had been dried by heating and provided with internal thermometer, stirrer bar, argon blanket and dropping funnel, and cooled to −75° C. 90 ml (144 mmol) of n-butyllithium (1.6M in hexane fraction) were added dropwise over the course of 30 minutes, and the mixture was subsequently stirred at this temperature for 1 h. 15.3 ml (18.3 g, 72 mmol) of diphenyldichlorosilane in 60 ml of THF were then added dropwise at −75° C., and the mixture was warmed to room temperature overnight. The solvent was removed, the residue was suspended in dichloromethane, and the mixture was filtered. The solvent was removed from the filtrate, and the product was recrystallised twice from butanol and twice from heptane/toluene, giving 16.8 g (47% of theory) in a purity of 99.9% according to HPLC. $^1$H-NMR (CDCl$_3$): [ppm]=7.51 (m, 8H), 7.55 (t, $^3J_{HH}$=7.7 Hz, 2H), 7.38 (m, 8H).

Example 2

Synthesis of the Comonomers for the Polymers

The synthesis of the further comonomers used is described in detail in WO 02/077060 and the literature cited therein. The monomer M1 used below is shown again here for reasons of clarity:

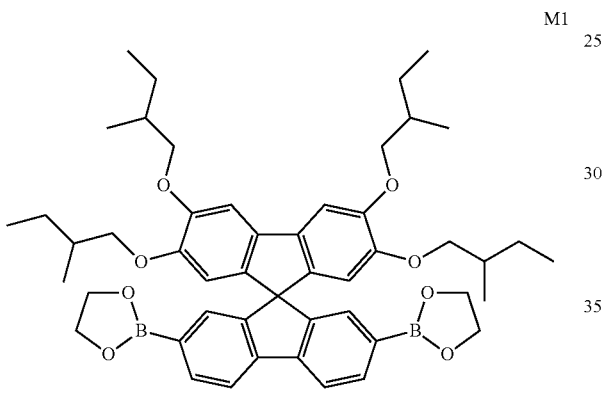

M1

Example 3

Synthesis of Polymer P1 (POLY1)

The synthesis was carried out by the process described in WO 03/048224. The following were employed: 1.6013 g (2 mmol) of monomer M1, 0.9886 g (2 mmol) of monomer Si1 and 2.03 g (2.2 equivalents) of potassium phosphate hydrate in 19 ml of dioxane, 6 ml of toluene and 12 ml of H$_2$O. The following were used as catalyst: 0.45 mg of Pd(OAc)$_2$ and 3.65 mg of P(o-tolyl)$_3$. Work-up gave 1.44 g of polymer which had a molecular weight M$_n$ of 57,000 and M$_w$ of 192,000 (GPC in THF with polystyrene standard). The synthesis of polymer P2 was carried out correspondingly.

Example 4

Structural Units TRIP1 for use in Blends

The compounds TRIP1 used here by way of example are derivatives of tris(phenylpyridyl)iridium(III). The synthesis of these compounds is described in WO 02/081488 and WO 04/026886. For clarity, the iridium complexes used here are shown again below:

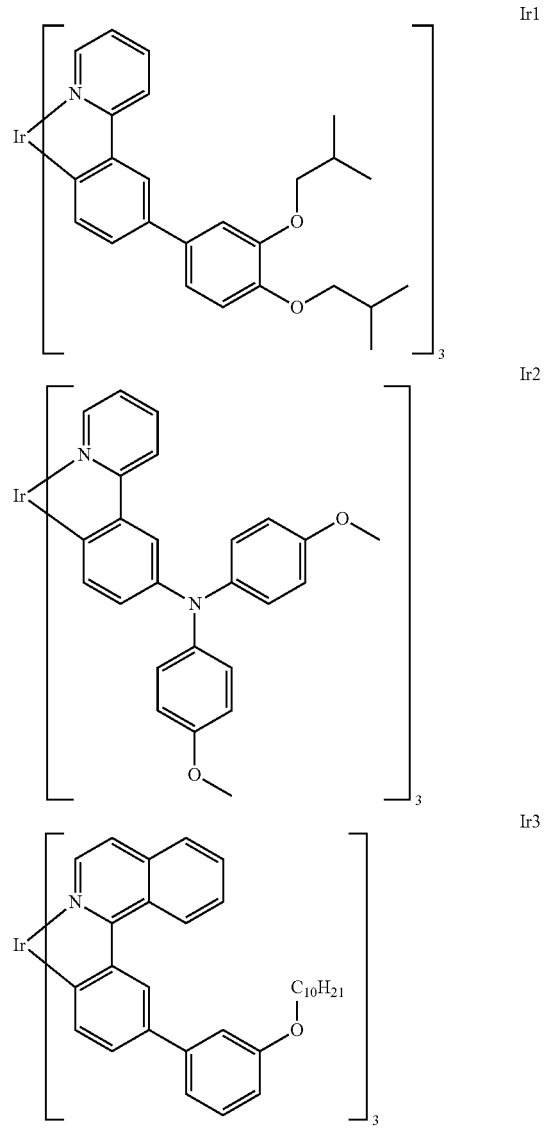

Example 5

Preparation of the Blends

The mixtures were prepared by dissolution of the blend constituents in the desired ratio and in the desired concentration in a suitable solvent. The solvent used here was toluene. The dissolution process here was carried out at 60° C. in an inert atmosphere. The solution was processed directly without isolation of the mixture (repeated precipitation of the solid components).

Example 6

Production of Polymeric Light-emitting Diodes (PLEDs)

The way in which PLEDs can be produced is described in detail in WO 04/037887 and the literature cited therein.

Example 7

Device Examples

Table 1 gives an overview of various blends of polymers, where in each case the composition of the polymers is also shown, and triplet emitters.

TABLE 1

Device results with blends according to the invention

| Blend | Polymer | Polymer composition | Triplet emitter[a] | Max. eff. | U @ 100 cd/m² | CIE x/y[b] | Lifetime (100)[c] |
|---|---|---|---|---|---|---|---|
| Blend 1 | P1 | 50% Si1, 50% M1 | 8% Ir1 | 20.7 cd/A | 6.9 V | 0.39/0.58 | 700 hrs |
| Blend 2 | P1 | 50% Si1, 50% M1 | 20% Ir1 | 23.4 cd/A | 5.3 V | 0.39/0.58 | 2000 hrs |
| Blend 3 | P1 | 50% Si1, 50% M1 | 8% Ir2 | 4.21 cd/A | 10.5 V | 0.60/0.40 | 100 hrs |
| Blend 4 | P1 | 50% Si1, 50% M1 | 20% Ir2 | 10.8 cd/A | 6.6 V | 0.62/0.38 | |
| Blend 5 | P2 | 10% Si1, 80% M1, 10% M2 | 20% Ir2 | 9.0 cd/A | 5.3 V | 0.62/0.38 | 64 hrs |
| Blend 6 | P1 | 50% Si1, 50% M1 | 8% Ir3 | 3.78 cd/A | 8.1 V | 0.68/0.32 | 90 hrs |
| Blend 7 | P1 | 50% Si1, 50% M1 | 20% Ir3 | 3.17 cd/A | 9.0 V | 0.68/0.32 | 110 hrs |
| Blend 8 | P2 | 10% Si1, 80% M1, 10% M2 | 8% Ir3 | 4.69 cd/A | 4.8 V | 0.68/0.32 | 1700 hrs |

[a]The concentration of the triplet emitter in the matrix is given in % by weight, i.e. 20% of triplet emitter in polymer P1 or P2 means 20 parts by weight of emitter and 80 parts by weight of P1
[b]CIE coordinates: chromaticity coordinates of the Commission Internationale de l'Eclairage from 1931
[c]The lifetime was extrapolated using an acceleration factor of 2 to a uniform initial luminous density of 100 cd/m².

The invention claimed is:

1. Mixtures comprising
   (A) at least one polymer comprising at least one structural unit which comprises at least one element from main group 4 (group 14 in accordance with IUPAC) other than carbon, and
   (B) at least one triplet emitter
   wherein said at least one structural unit comprises direct silicon-silicon or germanium-germanium bonds and/or
   at least one structural unit of the formulae (2), (3), and/or (4)

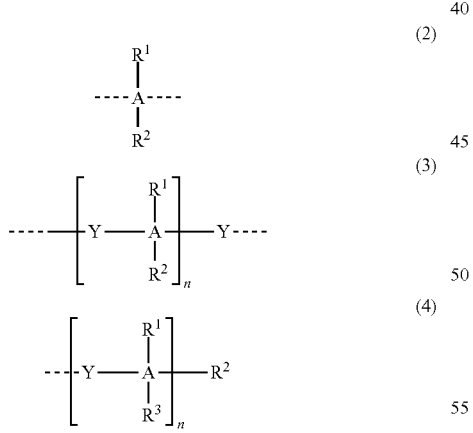

wherein:
A is on each occurrence, identically or differently, Si, Ge, Sn or Pb;
Y is on each occurrence, identically or differently, an aromatic or heteroaromatic ring system having up to 40 C atoms, which is optionally substituted by one or more radicals $R^4$, a vinyl group —$CR^4$=$CR^4$— or —$CR^4$=$C(R^4)_2$, an acetylene group —C≡C— or —C≡$CR^4$ or a combination of 2 to 5 of these groups;
$R^1$, $R^2$, and $R^3$ is on each occurrence, identically or differently, H, F, CN, $N(R^4)_2$, alkyl, alkoxy or thioalkoxy group having up to 40 C atoms which are optionally substituted by $R^4$, wherein one or more non-adjacent $CH_2$ groups are optionally replaced by —$R^5C$=$CR^5$—, —C≡C—, $Si(R^5)_2$, $Ge(R^5)_2$, $Sn(R^5)_2$, C=O, C=S, C=Se, C=$NR^5$, —O—, —S—, $NR^5$— or —$CONR^5$— and wherein one or more H atoms are optionally replaced by F, Cl, Br, I, CN, OH, $NO_2$, an aromatic or heteroaromatic ring system, or an aryloxy or heteroaryloxy group, in each case having up to 40 aromatic C atoms, wherein one or more H atoms are optionally replaced by F, Cl, Br, I, CN, OH, $NO_2$, one or more radicals $R^4$, or a combination of 2 to 5 of these systems; and wherein substituents $R^1$, $R^2$, and/or $R^3$ optionally define a further mono- or polycyclic, aliphatic or aromatic ring system with one another;
$R^4$ is on each occurrence, identically or differently, H, F, Cl, Br, I, CN, OH, $NO_2$, alkyl, alkoxy or thioalkoxy group having up to 22 C atoms wherein one or more non-adjacent C atoms are optionally replaced by —$R^5C$=$CR^5$—, —C≡C—, $Si(R^5)_2$, $Ge(R^5)_2$, $Sn(R^5)_2$, —$NR^5$—, —O—, —S—, —CO—O—, or —O—CO—O—, and wherein one or more H atoms are optionally replaced by F, Cl, Br, I, CN, OH, $NO_2$ or an aryl, heteroaryl or aryloxy group having up to 40 C atoms optionally substituted by one or more radicals $R^5$, OH, $N(R^5)_2$, $B(R^5)_2$ or $Si(R^5)_3$;
$R^5$ is on each occurrence, identically or differently, H or an aliphatic or aromatic hydrocarbon radical having up to 20 C atoms;
n is on each occurrence, identically or differently, 1, 2, 3, or 4; and wherein the dashed bond represents the link to the polymer;
wherein said at least one triplet emitter is mixed in said at least one polymer; and
wherein said at least one triplet emitter comprises at least one element from groups 8 to 10.

2. Mixtures according to claim 1, wherein said at least one polymer is conjugated or partially conjugated.

3. Mixtures according to claim 1, wherein A, identically or differently on each occurrence, is Si or Ge.

4. Mixtures according to claim 1, wherein Y, identically or differently on each occurrence, is an aromatic ring system having up to 40 C atoms which are optionally substituted by one or more radicals $R^4$, or a stilbene or tolan group which is optionally substituted by $R^4$.

5. Mixtures according to claim 1, wherein at least one of the substituents $R^1$, $R^2$, and $R^3$ is an aromatic or heteroaromatic ring system having up to 40 C atoms, which are optionally substituted by one or more substituents $R^4$.

6. Mixtures according to claim 1, wherein n, identically or differently on each occurrence, is 0, 1, or 2.

7. Mixtures according to claim 1, wherein said at least one structural unit of the formulae (2), (3), and/or (4) have a symmetrical structure.

8. Mixtures according to claim 1, wherein said at least one structural unit of the formulae (2), (3), and/or (4) are selected from Examples (1) to 33

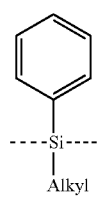

Example 1

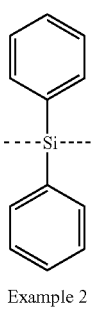

Example 2

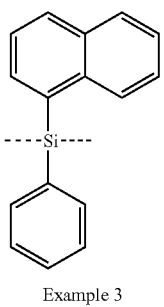

Example 3

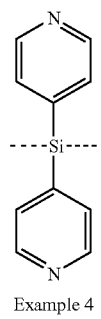

Example 4

Example 5

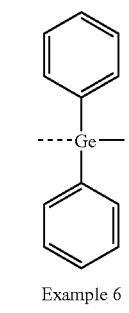

Example 6

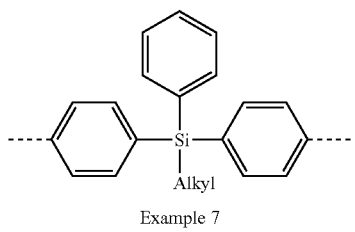

Example 7

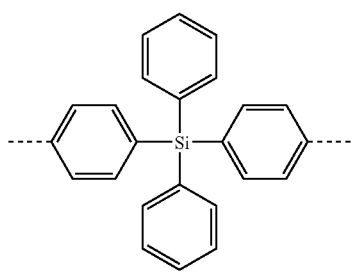

Example 8

-continued

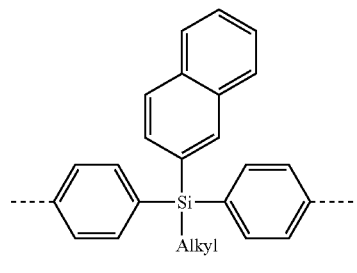

Example 9

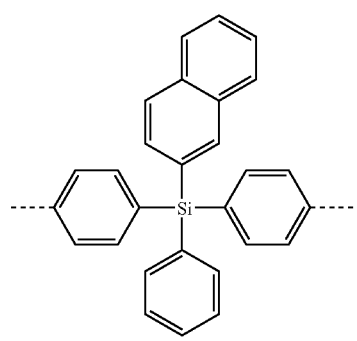

Example 10

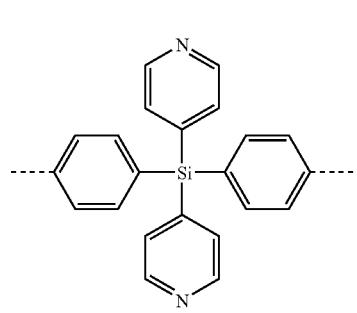

Example 11

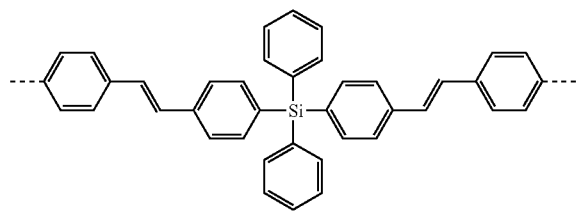

Example 12

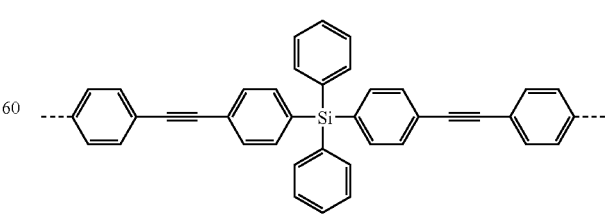

Example 13

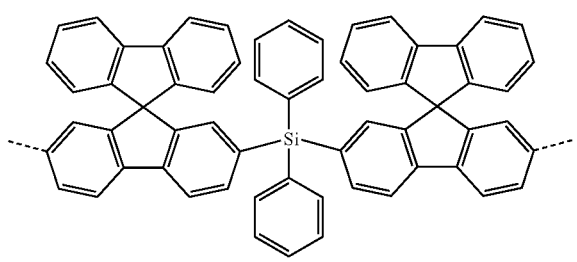
Example 14
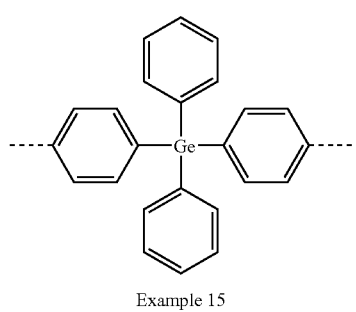
Example 15
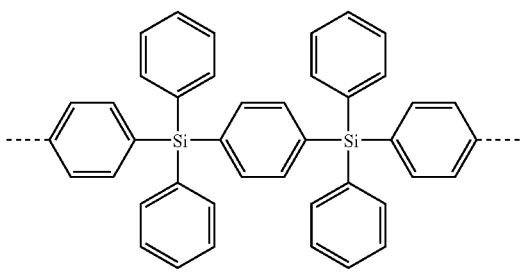
Example 16
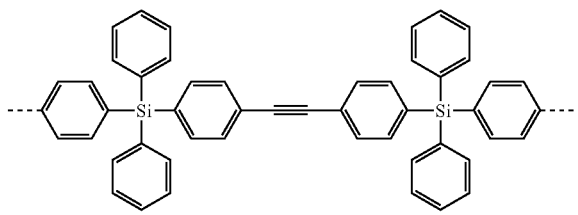
Example 17
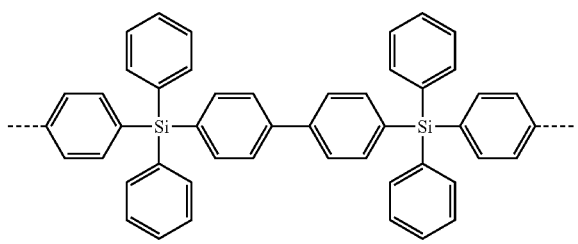
Example 18
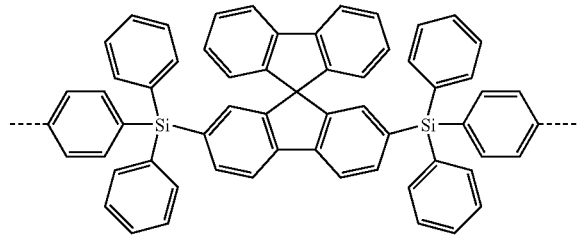
Example 19
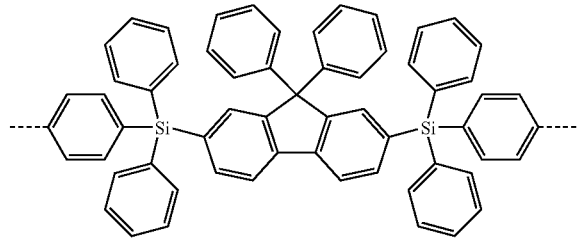
Example 20
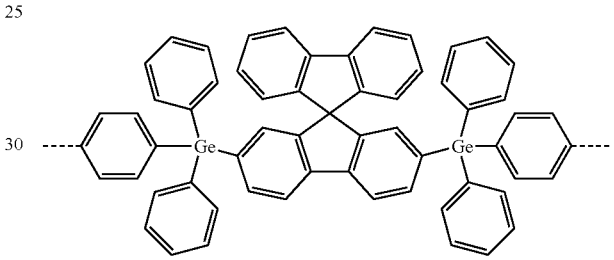
Example 21
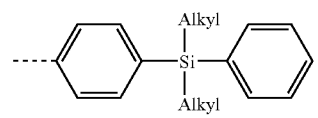
Example 22
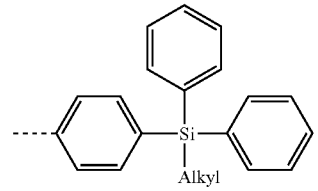
Example 23
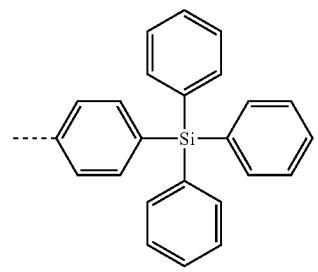
Example 24

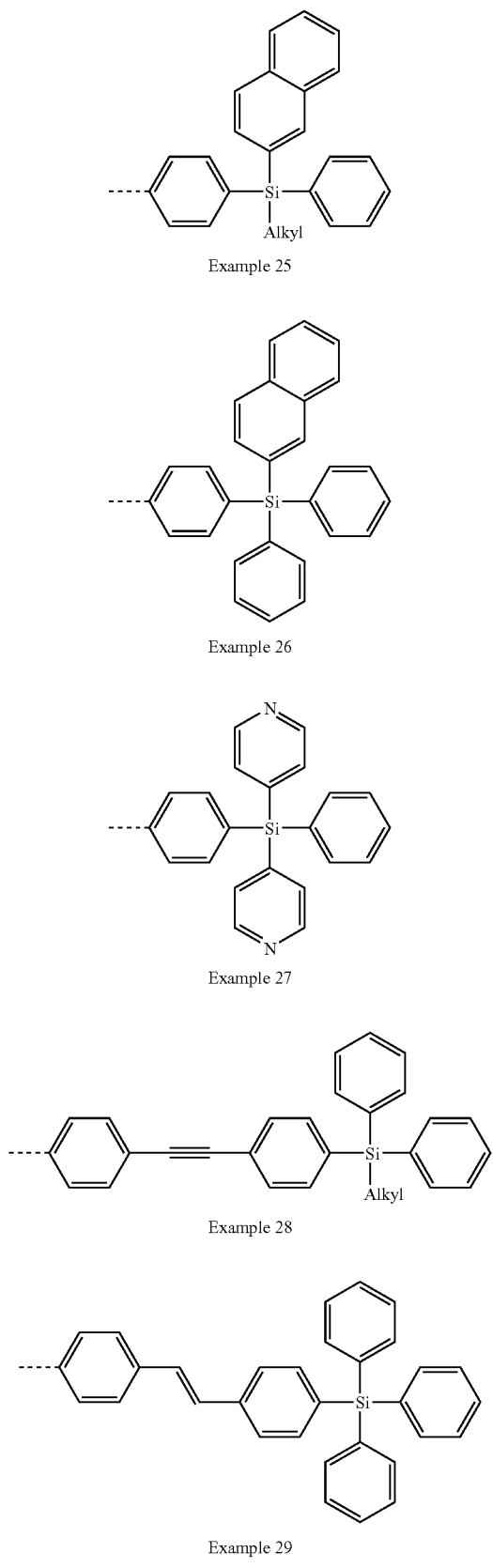
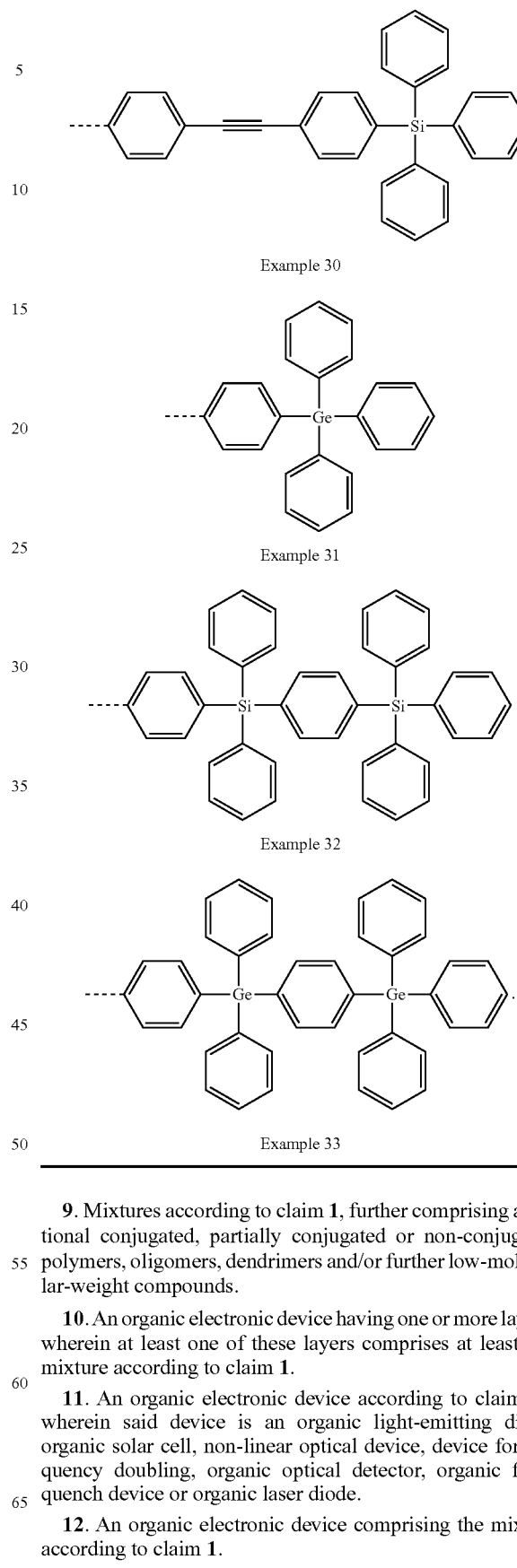

9. Mixtures according to claim 1, further comprising additional conjugated, partially conjugated or non-conjugated polymers, oligomers, dendrimers and/or further low-molecular-weight compounds.

10. An organic electronic device having one or more layers, wherein at least one of these layers comprises at least one mixture according to claim 1.

11. An organic electronic device according to claim 10, wherein said device is an organic light-emitting diode, organic solar cell, non-linear optical device, device for frequency doubling, organic optical detector, organic field-quench device or organic laser diode.

12. An organic electronic device comprising the mixture according to claim 1.

13. Mixtures comprising
(A) 5-99.9% by weight of at least one polymer comprising 1-100 mol % of one or more recurring units of formulae (2), (3), or (4)

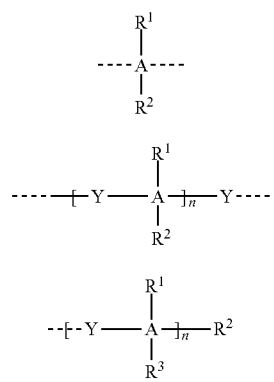

wherein
A is on each occurrence, identically or differently, Si, Ge, Sn or Pb;
Y is on each occurrence, identically or differently, an aromatic or hetero aromatic ring system having up to 40 C atoms, which is optionally substituted by one or more radicals $R^4$, a vinyl group —$CR^4$=$CR^4$— or —$CR^4$=$C(R^4)_2$, an acetylene group —C≡C— or —C≡$CR^4$ or a combination of 2 to 5 of these groups;
$R^1$, $R^2$, and $R^3$
is on each occurrence, identically or differently, H, F, CN, $N(R^4)_2$, alkyl, alkoxy or thioalkoxy group having up to 40 C atoms which are optionally substituted by $R^4$—, wherein one or more non-adjacent $CH_2$ groups are optionally replaced by —$R^5C$=$CR^5$—, —C≡C—, $Si(R^5)_2$, $Ge(R^5)_2$, $Sn(R^5)_2$, C=O, C=S, C=Se, C=$NR^5$, —O—, —S—, —$NR^5$— or —$CONR^5$— and wherein one or more H atoms are optionally replaced by F, Cl, Br, I, CN, OH, $NO_2$, an aromatic or heteroaromatic ring system, or an aryloxy or heteroaryloxy group, in each case having up to 40 aromatic C atoms, wherein one or more H atoms are optionally replaced by F, Cl, Br, I, CN, OH, $NO_2$, one or more radicals $R^4$, or a combination of 2 to 5 of these systems; and wherein substituents $R^1$, $R^2$, and/or $R^3$ optionally define a further mono- or polycyclic, aliphatic or aromatic ring system with one another;
$R^4$ is on each occurrence, identically or differently, H, F, Cl, Br, I, CN, OH, $NO_2$, alkyl, alkoxy or thioalkoxy group having up to 22 C atoms wherein one or more non-adjacent C atoms are optionally replaced by —$R^5C$=$CR^5$—, —C≡C—, $Si(R^5)_2$, $Ge(R^5)_2$, $Sn(R^5)_2$, —$NR^5$—, —O—, —S—, —CO—O—, or —O—CO—O—, and wherein one or more H atoms are optionally replaced by F, Cl, Br, I, CN, OH, $NO_2$ or an aryl, heteroaryl or aryloxy group having up to 40 C atoms optionally substituted by one or more radicals $R^5$, OH, $N(R^5)_2$, $B(R^5)_2$ or $Si(R^5)_3$;
$R^5$ is on each occurrence, identically or differently, H or an aliphatic or aromatic hydrocarbon radical having up to 20 C atoms;
n is on each occurrence, identically or differently, 1, 2, 3 or 4; and wherein the dashed bond represents the link to the polymer;
and
(B) 0.1-95% by weight of one or more triplet emitters, wherein said one or more triplet emitters comprises at least one element from groups 8 to 10.
14. Mixtures according to claim 13, wherein the proportion of the structural units of formulae (2), (3), and (4) in said polymer is in the range 5-80 mol %.
15. Mixtures according to claim 13, wherein said at least one polymer comprises further structural elements.
16. Mixtures according to claim 15, wherein said further structural elements form the polymer backbone or improve the charge-injection and/or charge-transport properties.
17. Mixtures comprising
(A) 0.5-99% by weight of at least one polymer comprising 0.1-100 mol % of one or more covalently bonded triplet emitters; and
(B) 1-99.5% by weight of at least one compound of formula (5)

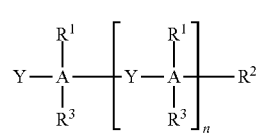

wherein
A is on each occurrence, identically or differently, Si, Ge, Sn or Pb;
Y is on each occurrence, identically or differently, an aromatic or hetero aromatic ring system having up to 40 C atoms, which is optionally substituted by one or more radicals $R^4$, a vinyl group —$CR^4$=$CR^4$— or —$CR^4$=$C(R^4)_2$, an acetylene group —C≡C— or —C≡$CR^4$ or a combination of 2 to 5 of these groups;
$R^1$, $R^2$, and $R^3$
is on each occurrence, identically or differently, H, F, CN, $N(R^4)_2$, alkyl, alkoxy or thioalkoxy group having up to 40 C atoms which are optionally substituted by $R^4$—, wherein one or more non-adjacent $CH_2$ groups are optionally replaced by —$R^5C$=$CR^5$—, —C≡C—, $Si(R^5)_2$, $Ge(R^5)_2$, $Sn(R^5)_2$, C=O, C=S, C=Se, C=$NR^5$, —O—, —S—, —$NR^5$— or —$CONR^5$— and wherein one or more H atoms are optionally replaced by F, Cl, Br, I, CN, OH, $NO_2$, an aromatic or heteroaromatic ring system, or an aryloxy or heteroaryloxy group, in each case having up to 40 aromatic C atoms, wherein one or more H atoms are optionally replaced by F, Cl, Br, I, CN, OH, $NO_2$, one or more radicals $R^4$, or a combination of 2 to 5 of these systems; and wherein substituents $R^1$, $R^2$, and/or $R^3$ optionally define a further mono- or polycyclic, aliphatic or aromatic ring system with one another;
$R^4$ is on each occurrence, identically or differently, H, F, Cl, Br, I, CN, OH, $NO_2$, alkyl, alkoxy or thioalkoxy group having up to 22 C atoms wherein one or more non-adjacent C atoms are optionally replaced by —$R^5C$=$CR^5$—, —C≡C—, $Si(R^5)_2$, $Ge(R^5)_2$, $Sn(R^5)_2$, —$NR^5$—, —O—, —S—, —CO—O—, or —O—CO—O—, and wherein one or more H atoms are optionally replaced by F, Cl, Br, I, CN, OH, $NO_2$ or an aryl, heteroaryl or aryloxy group having up to 40 C atoms optionally substituted by one or more radicals $R^5$, OH, $N(R^5)_2$, $B(R^5)_2$ or $Si(R^5)_3$;

$R^5$ is on each occurrence, identically or differently, H or an aliphatic or aromatic hydrocarbon radical having up to 20 C atoms;

n is on each occurrence, identically or differently, 0, 1, 2, or 3;

which is capable of forming glass-like layers at room temperature.

18. Mixtures according to claim 17, wherein the proportion of compounds of formula (5) in said mixture is in the range 5-80% by weight.

19. Mixtures comprising
(A) at least one polymer,
(B) at least one compound comprising at least one element from main group 4 (group 14 in accordance with IUPAC) other than carbon, and
(C) at least one triplet emitter
wherein said at least one compound comprises direct silicon-silicon or germanium-germanium bonds and/or
at least one compound of the formula (5)

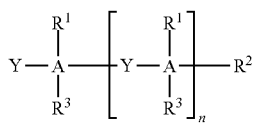

wherein:
A is on each occurrence, identically or differently, Si, Ge, Sn or Pb;

Y is on each occurrence, identically or differently, an aromatic or heteroaromatic ring system having up to 40 C atoms, which is optionally substituted by one or more radicals $R^4$, a vinyl group —$CR^4$=$CR^4$— or —$CR^4$=C$(R^4)_2$, an acetylene group —C≡C— or —C≡$CR^4$ or a combination of 2 to 5 of these groups;

$R^1$, $R^2$, and $R^3$
is on each occurrence, identically or differently, H, F, CN, $N(R^4)_2$, alkyl, alkoxy or thioalkoxy group having up to 40 C atoms which are optionally substituted by $R^4$, wherein one or more non-adjacent $CH_2$ groups are optionally replaced by —$R^5$C=$CR^5$—, —C≡C—, $Si(R^5)_2$, $Ge(R^5)_2$, $Sn(R^5)_2$, C=O, C=S, C=Se, C=$NR^5$, —O—, —S—, —$NR^5$— or —$CONR^5$— and wherein one or more H atoms are optionally replaced by F, Cl, Br, I, CN, OH, $NO_2$, an aromatic or heteroaromatic ring system, or an aryloxy or heteroaryloxy group, in each case having up to 40 aromatic C atoms, wherein one or more H atoms are optionally replaced by F, Cl, Br, I, CN, OH, $NO_2$, one or more radicals $R^4$, or a combination of 2 to 5 of these systems; and wherein substituents $R^1$, $R^2$, and/or $R^3$ optionally define a further mono- or polycyclic, aliphatic or aromatic ring system with one another;

$R^4$ is on each occurrence, identically or differently, H, F, Cl, Br, I, CN, OH, $NO_2$, alkyl, alkoxy or thioalkoxy group having up to 22 C atoms wherein one or more non-adjacent C atoms are optionally replaced by —$R^5$C=$CR^5$—, —C≡C—, $Si(R^5)_2$, $Ge(R^5)_2$, $Sn(R^5)_2$, —$NR^5$—, —O—, —S—, —CO—O—, or —O—CO—O—, and wherein one or more H atoms are optionally replaced by F, Cl, Br, I, CN, OH, $NO_2$ or an aryl, heteroaryl or aryloxy group having up to 40 C atoms optionally substituted by one or more radicals $R^5$, OH, $N(R^5)_2$, $B(R^5)_2$ or $Si(R^5)_3$;

$R^5$ is on each occurrence, identically or differently, H or an aliphatic or aromatic hydrocarbon radical having up to 20 C atoms;

n is on each occurrence, identically or differently, 0, 1, 2, or 3; and wherein said at least one compound and/or said at least one triplet emitter is mixed in said at least one polymer; and wherein said at least one triplet emitter comprises at least one element from groups 8 to 10.

20. Mixtures according to claim 19 comprising
(A) 0.5-98.5% by weight of at least one polymer;
(B) 1-99% by weight of at least one compound of formula (5)

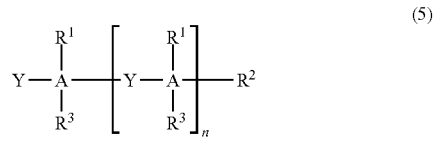

wherein
A is on each occurrence, identically or differently, Si, Ge, Sn or Pb;

Y is on each occurrence, identically or differently, an aromatic or hetero aromatic ring system having up to 40 C atoms, which is optionally substituted by one or more radicals $R^4$, a vinyl group —$CR^4$=$CR^4$— or —$CR^4$=C$(R^4)_2$, an acetylene group —C≡C— or —C≡$CR^4$ or a combination of 2 to 5 of these groups;

$R^1$, $R^2$, and $R^3$
is on each occurrence, identically or differently, H, F, CN, $N(R^4)_2$, alkyl, alkoxy or thioalkoxy group having up to 40 C atoms which are optionally substituted by $R^4$—, wherein one or more non-adjacent $CH_2$ groups are optionally replaced by —$R^5$C=$CR^5$—, —C≡C—, $Si(R^5)_2$, $Ge(R^5)_2$, $Sn(R^5)_2$, C=O, C=S, C=Se, C=$NR^5$, —O—, —S—, —$NR^5$— or —$CONR^5$— and wherein one or more H atoms are optionally replaced by F, Cl, Br, I, CN, OH, $NO_2$, an aromatic or heteroaromatic ring system, or an aryloxy or heteroaryloxy group, in each case having up to 40 aromatic C atoms, wherein one or more H atoms are optionally replaced by F, Cl, Br, I, CN, OH, $NO_2$, one or more radicals $R^4$, or a combination of 2 to 5 of these systems; and wherein substituents $R^1$, $R^2$, and/or $R^3$ optionally define a further mono- or polycyclic, aliphatic or aromatic ring system with one another;

$R^4$ is on each occurrence, identically or differently, H, F, Cl, Br, I, CN, OH, $NO_2$, alkyl, alkoxy or thioalkoxy group having up to 22 C atoms wherein one or more non-adjacent C atoms are optionally replaced by —$R^5$C=$CR^5$—, —C≡C—, $Si(R^5)_2$, $Ge(R^5)_2$, $Sn(R^5)_2$, —$NR^5$—, —O—, —S—, —CO—O—, or —O—CO—O—, and wherein one or more H atoms are optionally replaced by F, Cl, Br, I, CN, OH, $NO_2$ or an aryl, heteroaryl or aryloxy group having up to 40 C atoms optionally substituted by one or more radicals $R^5$, OH, $N(R^5)_2$, $B(R^5)_2$ or $Si(R^5)_3$;

$R^5$ is on each occurrence, identically or differently, H or an aliphatic or aromatic hydrocarbon radical having up to 20 C atoms;

n is on each occurrence, identically or differently, 0, 1, 2, or 3;

which is capable of forming glass-like layers at room temperature; and (C) 0.1-95% by weight of one or more triplet emitters.

* * * * *